United States Patent [19]
Neri et al.

[11] Patent Number: 5,404,023
[45] Date of Patent: Apr. 4, 1995

[54] DETECTION DEVICE, PARTICULARLY FOR SURFACE CHECKING CIGARETTES

[75] Inventors: Armando Neri, Bologna; Giancarlo Santin; Stefano Chini, both of San Lazzaro Di Savena, all of Italy

[73] Assignee: G.D Societa' Per Azioni, Bologna, Italy

[21] Appl. No.: 97,982

[22] Filed: Jul. 27, 1993

[30] Foreign Application Priority Data

Jul. 28, 1992 [IT] Italy .................. BO92A0287

[51] Int. Cl.⁶ .................................. G01N 21/88
[52] U.S. Cl. .................. 250/572; 250/223 R; 209/536
[58] Field of Search ............ 250/572, 223 R, 223 B, 250/562, 563; 356/237; 209/535, 536

[56] References Cited

U.S. PATENT DOCUMENTS

| | | | |
|---|---|---|---|
| 4,645,080 | 2/1987 | Scopatz | 250/223 R |
| 4,645,921 | 2/1987 | Heitmann et al. | 209/536 |

FOREIGN PATENT DOCUMENTS

| | | |
|---|---|---|
| 0977059 | 12/1964 | United Kingdom . |
| 2149101 | 6/1985 | United Kingdom . |
| WO89/05468 | 6/1989 | WIPO . |

*Primary Examiner*—David C. Nelms
*Attorney, Agent, or Firm*—Klauber & Jackson

[57] ABSTRACT

Cigarettes on a conveyor are surface checked, in at least one observation station, by means of at least one optical unit having a light source for directing light rays on to one half of the outer surface of the cigarette, and a pair of prismatic bodies facing respective quarters of the surface of the cigarette, and which provide for directing all the rays reflected from the aforementioned half of the surface into one beam directed towards one monitoring unit.

7 Claims, 1 Drawing Sheet

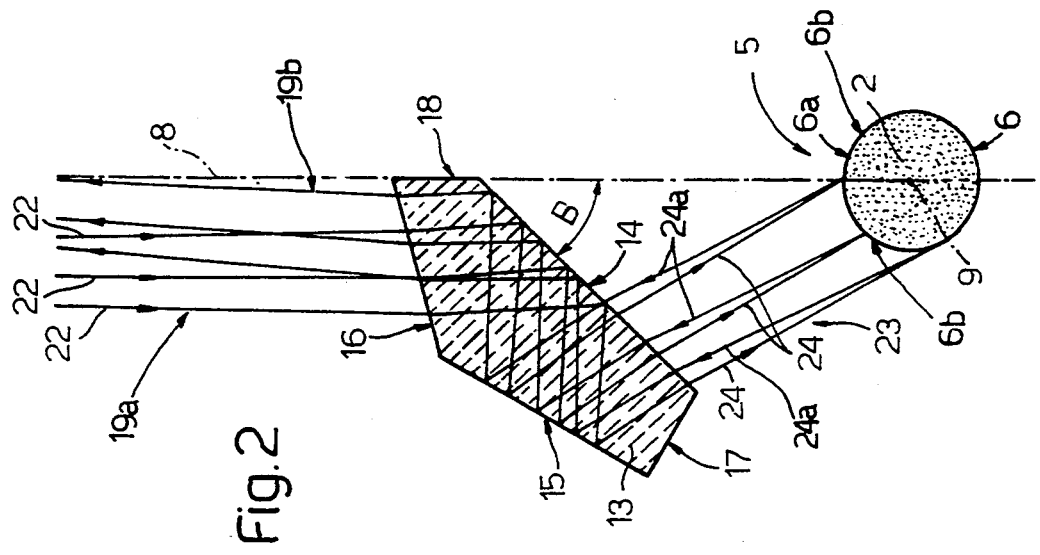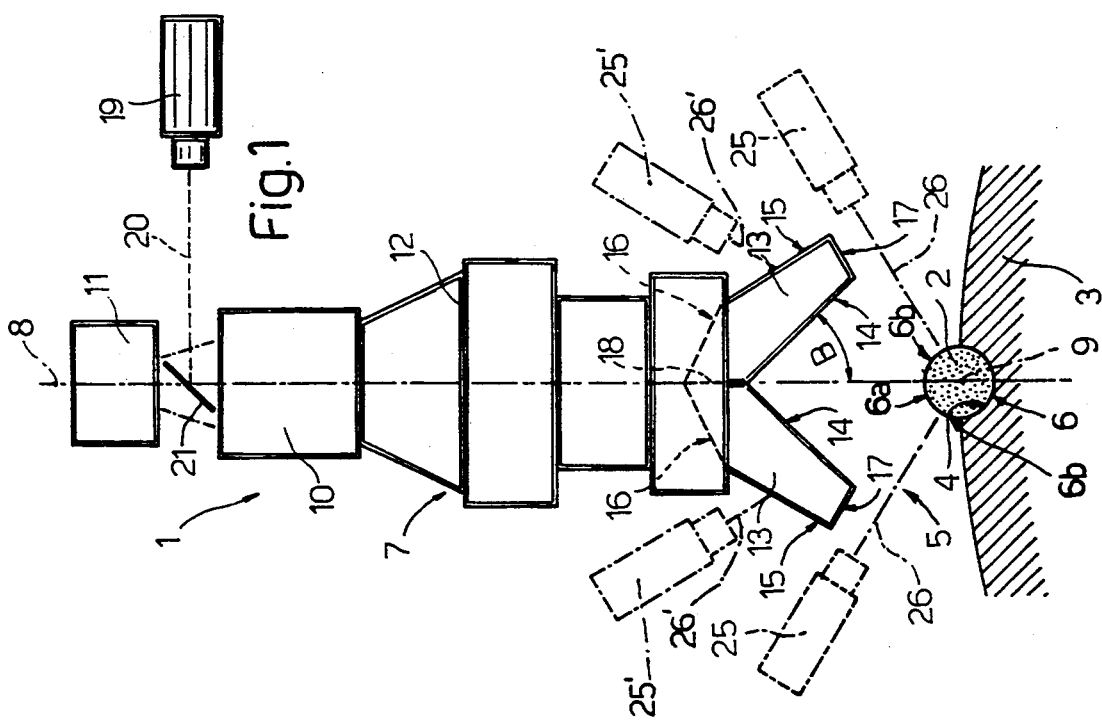

DETECTION DEVICE, PARTICULARLY FOR SURFACE CHECKING CIGARETTES

BACKGROUND OF THE INVENTION

The present invention relates to a detection device, particularly for surface checking cigarettes.

The surface quality of cigarettes coming off a production machine is normally checked by feeding the cigarettes successively through a detecting and monitoring device of the type described in U.S. Pat. No. 4,639,592. This comprises four separate optical units, each designed to detect surface flaws of various types on a respective quarter of the lateral surface of the cigarette, and each presenting a light source for directing a light beam on to the respective lateral surface quarter of the cigarette.

The light rays reflected by each surface quarter are concentrated by the respective optical unit into a beam, which is sent to a respective monitoring unit normally comprising a telecamera. This produces an image, which is compared, inside the monitoring unit, with a specimen image, and, in the event any major discrepancies are detected between the two images, a signal is emitted for rejecting the cigarette.

Though widely used and reliable enough from the operating standpoint, a major drawback of known detection devices of the aforementioned type is the relatively high cost, mainly due to featuring four monitoring units.

Moreover, by virtue of each surface quarter of the cigarette requiring both a light source and an optical unit, known detection devices of the aforementioned type are also relatively cumbersome and, hence, difficult to accommodate, for example, on filter assembly machines.

SUMMARY OF THE INVENTION

It is an object of the present invention to provide a detection device designed to overcome the aforementioned drawbacks, and which, in particular, is relatively cheap to produce and compact as compared with the above known devices.

A further object of the present invention is to provide a detection device designed to operate to a high degree of accuracy, and to supply the built-in detecting means with perfectly defined images.

According to the present invention, there is provided a detection device, particularly for surface checking cigarettes, the device comprising at least one optical unit for detecting the surface characteristics of a respective half of the lateral surface of the cigarette; and light ray emitting means for illuminating said half of said surface; characterized by the fact that said optical unit comprises one monitoring unit; and means for deflecting the rays reflected by respective portions of said half of said surface, and which provide for deflecting all the rays reflected by said half of said surface into one reflected beam directed towards said one monitoring unit.

According to a preferred embodiment of the present invention, said reflected ray deflecting means comprise two prismatic bodies facing respective surface quarters of the cigarette.

BRIEF DESCRIPTION OF THE DRAWINGS

A non-limiting embodiment of the present invention will be described by way of example with reference to the accompanying drawings, in which:

FIG. 1 shows a partial side view of a preferred embodiment of the device according to the present invention;

FIG. 2 shows a larger-scale detail of FIG. 1.

DETAILED DESCRIPTION OF THE INVENTION

Number 1 in FIG. 1 indicates a detection device for surface checking cigarettes 2 coming off a filter assembly machine (not shown).

Device 1 comprises a pair of parallel, counter-rotating rollers 3 (only one of which is shown partially in FIG. 1). Rollers 3 each present a number of peripheral seats 4 for partially accommodating respective cigarettes 2, and are each rotated about a respective axis (not shown) so as to successively feed cigarettes 2 through two observation stations 5 (only one shown), at each of which a respective longitudinal half 6a of the lateral surface 6 of cigarettes 2 is observed.

For each station 5, device 1 also comprises an optical unit 7 for observing and monitoring respective half 6a of surface 6. Each unit 7 presents an observation plane 8 containing the longitudinal axis 9 of cigarette 2 housed inside seat 4 in station 5, and which divides respective half 6a of surface 6 into two quarters 6b on either side of plane 8.

Unit 7 comprises focusing means consisting of a known spherical optical system 10 acting as a lens; a known monitoring unit 11 connected in known manner to spherical optical system 10; and an anamorphic optical unit 12, which, together with spherical optical system 10, constitutes a device for concentrating rays on to unit 11, and is located on the opposite side of spherical optical system 10 to unit 11, for adapting the dimensions of the image of cigarette 2 to spherical optical system 10, or more specifically, for better exploiting the detecting surface of the photosensitive element.

Unit 7 also comprises a pair of prismatic bodies 13 located on either side of plane 8 and facing respective quarters 6b of surface 6 of cigarette 2 in station 5.

Bodies 13 each present a longitudinal axis (not shown) parallel to axis 9, and a pentagonal cross section; diverge from anamorphic optical unit 12 towards seat 4; and are defined, on the side facing seat 4, by respective flat active surfaces 14 defining a dihedron with its edge lying in plane 8, and each forming the same angle B with plane 8. On the opposite side to surface 14, each body 13 is defined laterally by two flat surfaces 15 and 16 parallel to axis 9, sloping in relation to respective surface 14, converging outwards, and connected to respective surface 14 by two flat surfaces 17 and 18 also parallel to axis 9, and of which surface 18 lies substantially in plane 8 and is tangent to surface 18 of the other body 13.

Unit 7 also comprises a light source 19 for emitting a light beam 19a, which presents an axis 20 perpendicular to plane 8, and is so oriented as to impinge on a reflecting body 21 located between spherical optical system 10 and monitoring unit 11, for deflecting beam 19a (only half of which is shown in FIG. 2) in a direction parallel to plane 8, so that the rays 22 of beam 19a impinge on surface 16 of both bodies 13.

In actual use, as they travel through bodies 13, rays 22 of beam 19a are deflected and divided into two beams 23 (only one shown in FIG. 2), the rays 24 of each of which form a variable angle of other than zero with plane 8, so as to provide for optimum illumination of a respective quarter 6b of surface 6 under observation. The incident rays 24 of each beam 23 are then reflected by respective quarter 6b of surface 6 to form reflected rays 24a, each of which impinges on respective surface 14 with an angle of incidence within the cone of refraction. Rays 24a thus travel through respective surface 14, and, deflected simply by a given angle of refraction, impinge on respective surface 15, which is so oriented that rays 24a form, with a perpendicular to surface 15, an angle greater than the half angle of the refraction cone. As a result, rays 24a are reflected totally by respective surface 15 on to respective surface 14, which, like surface 15, reflects them totally on to respective surface 16 in a direction substantially parallel to plane 8. Since, as shown in FIG. 2, surface 16 forms an angle very close to 90° with plane 8, rays 24a are simply deflected by surface 16 by a given angle of refraction, and continue in a direction substantially parallel to plane 8 and perpendicular to axis 9. More specifically, rays 24a from both bodies 13 converge into one beam 19b (only half of which is shown in FIG. 2), which reaches monitoring unit 11 via anamorphic optical unit 12 and spherical optical system 10. As it travels through anamorphic optical unit 12, beam 19b is compressed in a direction parallel to axis 9, and expanded in a direction perpendicular to plane 8, so as to present a section better suited to unit 11 on leaving unit 12.

Unit 11 comprises, in known manner, a telecamera (not shown) or an array of photosensors, which, by means of beam 19b, is supplied with a composite image of the two quarters 6b of surface 6; and a known comparing device (not shown) in which the composite image is compared with a specimen image for detecting any discrepancies between the two. In the event discrepancies above a given threshold are detected, a signal is emitted in known manner for rejecting cigarette 2.

According to a first variation, source 19 may be replaced by two light sources 25 (25') as indicated by the dot-and-dash lines, and which, unlike source 19, illuminate respective quarters 6b of surface 6 directly (or via bodies 13) by emitting respective beams 26 (26').

Bodies 13, which are relatively straightforward and cheap to produce, therefore provide, not only for halving the number of monitoring units required and so drastically reducing production cost, but also for achieving a relatively compact device particularly suitable for use on a filter assembly machine.

It is claimed:

1. A detection device, particularly for surface checking cigarettes (2), the device comprising at least one optical unit (7) for detecting the surface characteristics of a respective half of the lateral surface (6) of the cigarette (2); and light ray emitting means (19; 25, 25') for illuminating said half of said surface (6); characterized by the fact that said optical unit (7) comprises one monitoring unit (11); and means (13) for deflecting the rays reflected by respective portions of said half of said surface (6), and which provide for deflecting all the rays reflected by said half of said surface (6) into one reflected beam directed towards said one monitoring unit (11).

2. A device as claimed in claim 1, characterized by the fact that said reflected ray deflecting means comprise two prismatic bodies (13) facing respective quarters of the surface (6) of the cigarette (2).

3. A device as claimed in claim 2, characterized by the fact that said two prismatic bodies (13) are substantially tangent to each other along a longitudinal plane (8) intersecting, in use, the axis of the cigarette (2) and dividing said half of said surface (6) into two quarters, and extend in diverging manner from opposite sides of said plane (8).

4. A device as claimed in claim 3, characterized by the fact that, on the side facing, in use, said cigarette (2), said prismatic bodies (13) are defined by respective flat active surfaces (14) forming a dihedron with its edge in said plane (8).

5. A device as claimed in claim 4, characterized by the fact that said active surfaces (14) slope by the same angle (B) in relation to said plane (8).

6. A device as claimed in claim 1, characterized by the fact that said optical unit (7) also comprises means (12) for concentrating said reflected beam on to said monitoring unit (11).

7. A device as claimed in claim 6, characterized by the fact that said concentrating means comprise anamorphic optical means (12) and image focusing means (10) arranged in series along said reflected beam.

* * * * *